(12) United States Patent
Colaco et al.

(10) Patent No.: US 10,240,179 B2
(45) Date of Patent: Mar. 26, 2019

(54) METHOD FOR THE PRODUCTION OF PROTEIN COMPLEXES AND VACCINE COMPOSITIONS COMPRISING THE SAME

(75) Inventors: Camilo Colaco, Cambridge (GB); Ian McEntee, Salisbury (GB)

(73) Assignee: Immunobiology Limited, Cambridge (GB)

( * ) Notice: Subject to any disclaimer, the term of this patent is extended or adjusted under 35 U.S.C. 154(b) by 0 days.

(21) Appl. No.: 14/006,586

(22) PCT Filed: Mar. 23, 2012

(86) PCT No.: PCT/GB2012/050650
§ 371 (c)(1),
(2), (4) Date: Oct. 7, 2013

(87) PCT Pub. No.: WO2012/127248
PCT Pub. Date: Sep. 27, 2012

(65) Prior Publication Data
US 2014/0017274 A1   Jan. 16, 2014

(30) Foreign Application Priority Data
Mar. 23, 2011   (GB) .................................. 1104897.2

(51) Int. Cl.
| | |
|---|---|
| *C12P 21/00* | (2006.01) |
| *A61K 39/00* | (2006.01) |
| *A61K 38/17* | (2006.01) |
| *A61K 39/04* | (2006.01) |
| *A61K 39/08* | (2006.01) |
| *A61K 39/09* | (2006.01) |
| *A61K 39/095* | (2006.01) |

(52) U.S. Cl.
CPC .......... *C12P 21/00* (2013.01); *A61K 38/1709* (2013.01); *A61K 39/0002* (2013.01); *A61K 39/0011* (2013.01); *A61K 39/04* (2013.01); *A61K 39/08* (2013.01); *A61K 39/092* (2013.01); *A61K 39/095* (2013.01)

(58) Field of Classification Search
None
See application file for complete search history.

(56) References Cited

U.S. PATENT DOCUMENTS

| | | | | |
|---|---|---|---|---|
| 5,827,685 | A * | 10/1998 | Lindquist | ..................... 435/69.1 |
| 5,935,576 | A | 8/1999 | Srivastava | |
| 6,048,530 | A | 4/2000 | Srivastava | |
| 2001/0041361 | A1 | 11/2001 | Dees et al. | |
| 2005/0175635 | A1 | 8/2005 | Colaco | |
| 2005/0232946 | A1 | 10/2005 | Colaco | |

FOREIGN PATENT DOCUMENTS

| | | | |
|---|---|---|---|
| WO | WO-95/24923 A2 | 9/1995 | |
| WO | WO-00/10597 A1 | 3/2000 | |
| WO | WO-01/013943 A2 | 3/2001 | |
| WO | WO-01/13944 A2 * | 3/2001 | |
| WO | WO 0163278 A2 * | 8/2001 | |
| WO | WO-0163278 A2 * | 8/2001 | .......... A61K 39/015 |
| WO | WO-02/20045 A2 | 3/2002 | |
| WO | WO-02/28407 A1 | 4/2002 | |
| WO | WO-2010/026432 A1 | 3/2010 | |
| WO | WO-2010026432 A1 * | 3/2010 | ......... A61K 39/0011 |
| WO | WO-2010146401 A1 | 12/2010 | |
| WO | WO-2011/033319 A1 | 3/2011 | |

OTHER PUBLICATIONS

Hecker et al. 1998 (Non-specific, general and multiple stress resistance of growth-restricted Bacillus subtilis cells by the expression of the oB regulon; Molecular Microbiology 29(5):1129-1136).*
Murphy et al. 1999 (Emergence of *Saccharomyces cerevisiae* as a human pathogen: Implications for biotechnology; Enzyme and Microbial Technology 25:551-557) teach *S. cerevisiae* is a fungus and causes systemic and superficial diseases in humans (p. 552, sections 3 and 4).*
Wang et. al. 2006 (Recent advances in heat shock protein-based cancer vaccines; Hepatobiliary & Pancreatic Diseases International; 5(1): 22-27).*
Abcam 2015 (http://docs.abcam.com/pdf/protocols/general-western-blot-protocol.pdf; Jul. 1, 2015).*
Nover 1991 (Inducers of HSP Synthesis: Heat Shock and Chemical Stressors; in Heat Shock Response; CRC Press; ISBN 0-8493-4912-5).*
Svensater et al. 2000 (Multiple stress responses in *Streptococcus mutans* and the induction of general and stress-specific proteins; Microbiology 146: 107-117).*
Zeng et al 2006 (Chaperone-rich cell lysates, immune activation and tumor vaccination; Cancer Immunol Immunother 55: 329-338). (Year: 2006).*
Hecker et al. 1998 (Molecular Microbiology 29(5):1129-1136 (Year: 1998).*
Heikkila, J.J. et al., "Heat and sodium arsenite act synergistically on the induction of heat shock gene expression in Xenopus laevis A6 cells", Biochemistry and Cell Biology. 1987, vol. 65, No. 4, pp. 310-316.
Bassias, Ioannis, "International Search Report," for PCT/GB2012/050650 dated May 29, 2012, 4 pages.
Pockley, A. G., "Heat Shock Proteins as Regulators of the Immune Response," The Lancet, vol. 362, No. 9382, Aug. 9, 2003, pp. 469-476.

(Continued)

*Primary Examiner* — Mary Maille Lyons
(74) *Attorney, Agent, or Firm* — Winstead PC

(57) ABSTRACT

The present invention relates to methods for the production of heat shock protein complexes for use in vaccine compositions. In particular, there is provided a method for increasing the level and immunogenicity of heat shock protein complexes produced in cells by subjecting the cells to specific stress inducing stimuli. The invention further extends to the use of heat shock protein complexes produced according to the methods of the invention in the preparation of vaccine compositions for the prevention and treatment of infectious diseases and cancerous conditions.

23 Claims, 9 Drawing Sheets

(56) References Cited

OTHER PUBLICATIONS

Vanbogelen, Ruth A., "Differential Induction of Heat Shock, SOS, and Oxidation Stress Regulons and Accumulation of Nucleotides in *Escherichia coli*," Journal of Bacteriology, Jan. 1987, pp. 26-32.
Clark, T. A., et al., "Automatic Control of Dissolved Oxygen Tension via Fermenter Agitation Speed," Biotechnology and Bioengineering, vol. XVII, pp. 1507-1511 (1985).
Aravindhan, Vivekanandan, et al., "*Mycobacterium Tuberculosis groE* Promoter Controls the Expression of the Bicistronic *groESL1* Operon and Shows Differential Regulation Under Stress Conditions," FEMS Microbiol. Lett. 292 (2009) pp. 42-49.
Colaco, Camilo, et al., "BCG (Bacille Calmette-Guérin) HspCs (heat-shock protein-peptide complexes) induce T-helper 1 responses and protect against live challenge in a murine aerosol challenge model of pulmonary tuberculosis", Biochemical Society Transactions (2004) vol. 32, part 4, pp. 626-628.
Bacon, Joanna, et al., "Transcriptional Responses of *Mycobacterium tuberculosis* Exposed to Adverse Conditions In Vitro", Current Molecular Medicine 2007, 7, pp. 277-286.
Wilks, Jessica C., et al., "Acid and Base Stress and Transcriptomic Responses in *Bacillus subtilis*", Applied and Environmental Microbiology, Feb. 2009, vol. 75, No. 4, pp. 981-990 (Published ahead of print, Dec. 29, 2008).
Holmes, Christopher W., et al., "The *hrcA* and *hspR* regulons of *Campylobacter jejuni", Microbiology* (2010),156, pp. 158-166.
Bucca, Giselda, et al., "Negative feedback regulation of *dnaK, clpB* and *Ion* expression by the DnaK chaperone machine in *Streptomyces coelicolor*, identified by transcriptome and in vivo DnaK-depletion analysis", Molecular Microbiology (2003) 50(1), pp. 153-166.

* cited by examiner

Osmotic stress

Acid stress

METHOD FOR THE PRODUCTION OF PROTEIN COMPLEXES AND VACCINE COMPOSITIONS COMPRISING THE SAME

FIELD OF THE INVENTION

The present invention relates to methods for the production of heat shock protein complexes. The invention further extends to the use of heat shock protein complexes produced according to the methods of the invention in the preparation of vaccine compositions for the prevention and treatment of infectious diseases and cancerous conditions.

BACKGROUND OF THE INVENTION

Heat shock proteins (hsps, HSPs) are a family of highly conserved proteins that are widely distributed throughout the plant and animal kingdoms. On the basis of their molecular weight, the major heat shock proteins are grouped into six different families: small (hsp20-30 kDa); hsp40; hsp60; hsp70; hsp90; and hsp100. Heat shock proteins are ubiquitously expressed in both prokaryotic and eukaryotic cells, where they function as chaperones in the folding and unfolding of polypeptides. A further role of heat shock proteins is to chaperone peptides from one cellular compartment to another and, in the case of diseased cells, heat shock proteins are also known to chaperone viral or tumour-associated peptides to the cell-surface for presentation to the immune system.

Although heat shock proteins were originally identified in cells subjected to heat stress, their production can result from a number of other forms of stress, such as infection, osmotic stress, cytokine stress and the like. Accordingly, heat shock proteins are also commonly referred to as stress proteins (SPs) on the basis that their expression is not solely caused by a heat stress. However, transcriptional analysis of the genes induced by different stress stimuli show the induction of distinct sets of genes following exposure of a cell to different stress inducing stimuli (Bacon & Marsh (2007) *Curr. Mol. Med.* 7:277-86). Moreover, the individual stress regulons are independently induced (vanBogelen et al. (1987) *J. Bact.* 169:26-32 and Wilkes et al. (2009) *Applied and Environmental Microbiol.* 75:981-990) and regulated (Holmes et al. (2010) *Microbiology* 156:158-166). In particular, vanBogelen shows that different stress inducing stimuli cause distinct heat shock protein genes to be expressed and that the specific expression of these genes resulted only from one type of stress inducing stimulus when four stress inducing stimuli were tested.

While heat shock proteins can themselves be used as the immunogenic determinant in vaccine compositions, it has been observed that complexes formed between heat shock proteins and peptides, in particular antigenic peptide fragments, mediate an enhanced immune response when administered to a subject. Furthermore, it is known that heat shock proteins can produce complexes which can be classed as either constitutively produced heat shock protein complexes or induced heat shock protein complexes. Constitutively produced heat shock protein complexes are those comprising heat shock proteins which are produced under normal homeostatic conditions. Induced heat shock protein complexes are produced when a cell is exposed to conditions of stress. When in a stressed state, the cell upregulates the production of stress proteins, with these upregulated heat shock proteins being known as induced heat shock proteins. Furthermore, these induced heat shock proteins form complexes with peptide fragments which are seen to be more immunogenic than complexes formed when a cell is not under conditions of stress. The enhanced immunogenicity of such induced heat shock protein complexes over constitutive heat shock protein complexes has been exemplified in WO 01/13943. Without wishing to be bound by theory, the inventors predict that the enhanced immunogenicity observed with induced heat shock protein complexes is not due to the actual stress protein component of the complex being different, but due to the stress conditions causing proteins within the cell to unfold or denature. The heat shock proteins therefore complex with proteins or protein fragments to prevent them unfolding, or to refold them, as well as complexing with protein fragments as part of the cell's antigen processing pathway.

Vaccine compositions which comprise heat shock protein complexes (which may also be referred to as stress protein complexes) as the immunogenic determinant are widely known. Such vaccines have significant potential as they show the promise of conferring broad, protective immunity against infection and disease. It has also been widely documented that heat shock protein complexes are efficacious as vaccines against specific cancers. It has been shown that pathogen derived stress protein complexes isolated from heat-shocked BCG cells induced T-helper 1 (Th1) lymphocyte mediated immune responses in a vaccinated host, Which conferred protective immunity against a live challenge in a murine aerosol challenge model of pulmonary tuberculosis (International PCT Patent Application No. WO 01/13944). Moreover, it has been shown in WO 02/20045, WO 00/10597 and WO 01/13943 that stress protein complexes isolated from pathogens or pathogen infected cells are effective as the immunogenic determinant within vaccines against infectious diseases.

There have been various approaches to producing vaccine compositions comprising stress protein complexes for the treatment and prevention of infectious diseases. WO 95/24923 discloses constitutive heat shock protein complexes comprising a heat shock protein derived from a host eukaryotic cell and an antigenic peptide fragment derived from a pathogen. WO 01/13943 discloses heat shock protein complexes which are induced following the use of a stress inducing stimulus such as heat or a cytokine such as tumour necrosis factor (TNF). Said stress proteins may comprise stress proteins derived from a host cell, or, alternatively, stress proteins derived from an invading pathogen, said stress proteins being complexed to a peptide derived from the invading pathogen. WO 01/13944 discloses stress protein complexes which are produced following a pathogen being subjected to a stress inducing stimulus, wherein the stress protein and associated peptide fragment are derived directly from the pathogen.

SUMMARY OF THE INVENTION

Following extensive experimentation, the inventors have surprisingly observed that the production of induced heat shock protein complexes using a plurality of stress inducing stimuli, typically heat stress and respiratory stress or heat stress and acid based stress, enhances the quantum of induced stress protein complexes produced in a cell, when compared to induced stress protein complexes produced following exposure to a single type of stress inducing stimulus. Specifically, the inventors have observed that the amount of heat shock protein-peptide complexes (HspCs) which are produced following the exposure of a cell or cells to multiple stress stimuli can result in a four-fold increase in the number of heat shock protein-peptide complexes produced. The production of a higher yield of heat shock protein-peptide complexes is of significant commercial relevance as large quantities of heat shock protein complexes would be required for large scale production of a prophylactic or therapeutic vaccine. Moreover, the inventors have also surprisingly identified that the induced heat shock protein-peptide complexes produced using a plurality of stress inducing stimuli, such as heat stress and respiratory stress or heat stress and acid based stress, are more immunogenic than induced heat shock protein complexes produced using only a single stress inducing stimulus, such as heat shock alone.

According to a first aspect of the present invention there is provided a method for the production of stress protein complexes formed between a stress protein and a peptide, said method comprising, consisting of, or consisting essentially of the steps of:
culturing cells,
exposing said cells to a plurality of stress inducing stimuli, and
purifying the stress protein complexes from the cells.

In certain embodiments, the peptide is a peptide fragment. In certain embodiments, the peptide is an antigenic peptide or an antigenic peptide fragment. In certain embodiments, the peptide is derived from a pathogenic organism which typically causes an infectious disease, e.g. a prokaryotic organism (e.g. gram positive bacteria or gram negative bacteria), protozoa, a virus, a parasite or fungi.

In certain embodiments wherein the peptide is derived from bacteria, the bacteria are selected from the group consisting of *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*.

In certain embodiments wherein the peptide is derived from a virus, the virus is selected from the group consisting of human immunodeficiency virus, hepatitis A virus, hepatitis B, hepatitis C, human papillomavirus, Kaposi's Sarcoma-Associated Herpesvirus, Herpes Simplex virus, Respiratory Syncytial Virus, Ebola virus, Marburg virus, West Nile virus, St Louis Encephalitis virus, Rift Valley Fever virus, Influenza viruses, corona virus, rhinovirus, adenovirus, SIV, rotavirus, human papilloma virus, arbovirus, measles virus, polio virus, rubella virus, mumps virus, papova virus, varicella-zoster virus, varicella virus, huntavirus and cytomegalovirus.

In certain embodiments, the peptide is a tumour specific antigen.

In certain embodiments, exposing the cells to the plurality of stress inducing stimuli comprises exposing the cells to at least two stress inducing stimuli. Typically, the cells are exposed to two stress inducing stimuli of different types, but may be exposed to three or more stress inducing stimuli of different types. In certain embodiments, the stress inducing stimuli can be selected from the group consisting of, but not limited to, heat stress, respiratory stress (oxygen starvation or addition), oxidative stress ($H_2O_2$, Fe), acid based stress such as pH change, heavy metal stress, osmotic stress, metabolite restriction and nutrient starvation such as carbon or iron limitation. In certain preferred embodiments, the stress inducing stimuli is heat stress and at least one of respiratory stress, oxidative stress ($H_2O_2$, Fe), acid based stress (pH4), heavy metal stress, osmotic stress, metabolite restriction or nutrient starvation such as carbon or iron limitation, and in particular may be heat stress and respiratory stress or heat stress and acid based stress. Typically the at least two stress inducing stimuli are applied to the cells sequentially. In certain embodiments, the at least two stress inducing stimuli are applied sequentially.

In certain embodiments, the present invention therefore provides a method for the production of complexes formed between a stress protein and an antigenic peptide, said method comprising, consisting of, or consisting essentially of the steps of:
culturing cells,
exposing said cells to a heat stress,
exposing said cells to a respiratory stress; and
purifying the heat shock protein complexes from the cells.

Typically said cells are exposed to the heat stress and the respiratory stress simultaneously.

In alternative embodiments, the present invention provides a method for the production of complexes formed between a stress protein and an antigenic peptide, said method comprising, consisting of, or consisting essentially of the steps of:
culturing cells,
exposing said cells to a heat stress,
exposing said cells to an acid based stress, and
purifying the heat shock protein complexes from the cells.

Typically said cells are exposed to the heat stress and acid based stress simultaneously, that is, the cells are exposed to the heat stress and the acid based stress at the same time.

In certain embodiments, the heat stress or heat shock comprises increasing the heat to which the cultured cells are exposed to a temperature of around 5° C. to 10° C. above the normal growth temperature of the cells. Accordingly, if the cells are typically grown at 37° C., then the heat stress may comprise increasing the temperature to which the cells are exposed to about 44° C. In certain embodiments, said temperature increase is achieved by raising the temperature within a fermenter, which may be used, for example, to cultivate the cultured cells to around 42° C. to 44° C. In certain embodiments, the temperature increase is achieved by increasing the temperature from the normal growth temperature at a rate of between or around 0.25° C. to 0.5° C. per minute (0.25-0.5° C./min). In certain embodiments, the cells are subjected to a heat stress for a time period ranging from around 30 minutes to 2.5 hours. In certain embodiments, the heat stress may typically occur for between 1 to 2 hours.

In certain embodiments, the respiratory stress relates to decreasing the amount of oxygen to which the cultured cells are exposed. Typically, this comprises restricting the supply of oxygen to the cultured cells from that which causes the normal physiological growth or homeostasis of the cells. In certain embodiments, this can be achieved by removing the dissolved oxygen tension (DOT) cascade control as the temperature of the culture increases. In a preferred embodiment the dissolved oxygen tension can be further limited by manually reducing the agitation rate, for example, to approximately 320 to 350 rpm. Clark et al., (1985) *Biotechnology and Bioengineering*, 27:1507-1511 describes how the dissolved oxygen tension can be controlled in a fermenter via the agitation rate. In a further embodiment, oxygen limitation is achieved by its partial or complete replacement with carbon dioxide or nitrogen. In certain preferred embodiments, the respiratory stress is applied to the cells in a fermenter. In certain embodiments, the respiratory stress relates to increasing the amount of oxygen to which the cultured cells are exposed.

In certain embodiments, the acid based stress or acid stress comprises reducing the pH of the cultured cells to a pH below the normal pH at which the cells are cultured, the normal pH being the pH which causes normal physiological growth or homeostasis of the cells. In certain embodiments, the pH is lowered to 5.5, 5, 4.5 or 4. The pH may be lowered by adding an acid, e.g. hydrochloric acid to the cells. In certain embodiments, the acid based stress is applied to the cells in a fermenter.

The cells may be exposed to the plurality of stress inducing stimuli simultaneously or sequentially. Accordingly, in certain embodiments, the cells are subjected to the heat stress prior to being exposed to a second stress, such as the respiratory stress or acid based stress. In a further embodiment, the cells are subjected to the heat stress and to a second stress, such as the respiratory stress or acid based stress, concurrently. In a further embodiment, the cells may be subjected to another stress such as the respiratory stress or acid based stress first and then subjected to the heat stress.

A preferred combination of stresses can be determined by using standard methods to apply stress inducing stimuli and then quantitating the induction of stress proteins, such as GroEL and DnaK. Typically the preferred combination of stresses increases the induction of both GroEL and DnaK. Standard methods which may be used to quantitate the induction of stress proteins include protein gel analysis, densitometry, immunoblotting and ELISA.

Pathogenic Cells

In certain embodiments, the cells are pathogenic cells. In certain embodiments, the pathogenic cells are non-mammalian cells, in particular prokaryotic cells which may be gram positive or gram negative bacteria. In certain further embodiments, the pathogenic cells are microbial cells, protozoan cells or parasitic cells.

In certain embodiments, the prokaryotic cells are bacteria selected from the group consisting of, but not limited to: *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*.

In certain embodiments, the bacteria are selected from the group consisting of *Neisseria* (e.g. *N. meningitidis* MC58), *Mycobacteria, Clostridium* (e.g. *Clostridium difficile*), *Saccharomyces* (e.g. *S. cerevisiae*) and *Streptococcus*, e.g. *S. pneumoniae*. A combination of heat stress and respiratory stress has been shown to result in higher levels of production of stress protein complexes in *Neisseria, Mycobacteria, Saccharomyces* and *Clostridium* when compared to stress protein complexes obtained from cells exposed to only one type of stress inducing stimulus. Accordingly, in certain embodiments the cells are *Neisseria* (e.g. *N. meningitidis* MC58), *Mycobacteria, Saccharomyces* (e.g. *S. cerevisiae*) or *Clostridium* (e.g. *Clostridium difficile*) and the plurality of stress inducing stimuli comprises heat stress and respiratory stress. A combination of heat stress and acid based stress has been shown to result in higher levels of production of stress protein complexes in *S. pneumoniae* when compared to stress protein complexes obtained from cells exposed to only one type of stress inducing stimulus. Accordingly, in certain embodiments the cells are *Streptococcus*, e.g., *S. pneumoniae*, and the plurality of stress inducing stimuli comprises heat stress and acid based stress. The stress protein complexes obtained from cells exposed to two different types of stress inducing stimuli also show improved immunogenicity when compared to stress protein complexes obtained from cells exposed to only one type of stress inducing stimulus.

Aerobic Cells

In certain embodiments, the cells are aerobic cells, for example pathogenic aerobic cells. During the normal growth of cells in culture, the cells will have an optimum requirement for oxygen. For example, an aerobic cell will require oxygen for growth and survival. The depletion of the oxygen level will limit the ability of an aerobic cell to grow. The absence of oxygen in the growth medium will most likely result in the death of the cell. Any particular cell will have a preferred dissolved oxygen tension (DOT), this being the oxygen supply provided to the growing and stationary cells in culture. For example, a cell culture may be grown with a dissolved oxygen tension (DOT) at a range of between >10% to 50%. In certain preferred embodiments, the dissolved oxygen tension (DOT) may be provided at a level of, or around >20% or of about >30%.

Facultative Anaerobic Cells

In certain embodiments, the cells are facultative anaerobic cells, for example pathogenic anaerobic cells. A facultative anaerobic organism is an organism which usually makes ATP by aerobic respiration. However, when oxygen is not present, the facultative anaerobe can switch to fermentation. Facultative anaerobes therefore survive in the presence of oxygen, while obligate anaerobes die. Further, the concentration of oxygen and fermentable material in the growth environment will influence whether the facultative anaerobe uses aerobic respiration or fermentation to derive energy. The depletion of the oxygen level will therefore limit the ability of a facultative anaerobe to grow. However, the absence of oxygen in the growth medium or environment may result in a switch to anaerobic growth. Accordingly, exposing a facultative anaerobic cell to respiratory stress will involve carefully managing the dissolved oxygen tension (DOT) to which the cells are exposed in order to induce respiratory stress. The application of respiratory stress may also involve the removal of fermentable material from the growth environment.

Anaerobic Cells

In certain embodiments, the cells are anaerobic cells, for example pathogenic anaerobic cells. In a certain embodiment of the invention, stress protein complexes may be derived from anaerobic pathogens (obligate anaerobes), in particular anaerobic bacteria, which cannot grow in the presence of oxygen.

Accordingly, the application of respiratory stress to obligate anaerobes requires oxygen to be added to the culture medium, rather than removed, in order to confer an oxidative stress linked stress inducing stimulus. Accordingly, an anaerobic cell culture may be exposed to respiratory stress by growing it in the presence of a dissolved oxygen tension (DOT) at a range of between >10% to 50%. In certain preferred embodiments, the dissolved oxygen tension (DOT) may be provided at a level of, or around >20% or of about >30%.

Accordingly, in certain embodiments the method comprises a method for the production of complexes formed between a stress protein and an antigenic peptide or antigenic peptide fragment which is derived from an anaerobic pathogen, said method comprising, consisting of, or consisting essentially of the steps of:

culturing anaerobic pathogenic cells in an environment in which oxygen is not present, exposing said cells to a heat stress, further exposing said cells to a respiratory stress, said stress comprising increasing the amount of oxygen to which the cultured cells are exposed, and purifying the stress protein complexes from the anaerobic pathogenic cells.

In certain embodiments, said cells are exposed to the heat stress and respiratory stress simultaneously, that is, the cells are exposed to the heat stress and the acid based stress at the same time.

In certain embodiments, nitrogen may be present in the culture medium to compensate for the lack of oxygen.

Cancerous Cells

In certain embodiments, the cells are cancerous cells. Accordingly in certain embodiments the present invention provides a method for the production of complexes formed between a stress protein and an antigenic peptide, said method comprising, consisting of, or consisting essentially of the steps of:

culturing cancerous cells, exposing said cells to a heat stress, exposing said cells to a respiratory stress or an acid based stress, and purifying the heat shock protein complexes from the cancerous cells.

Typically said cells are exposed to the heat stress and the acid based stress or respiratory stress simultaneously, that is, the cells are exposed to the heat stress and the acid based stress at the same time.

Genetically Modified Cells

In certain embodiments, the invention extends to a cell or cells which have been genetically modified to constitutively express heat shock proteins, e.g. by deleting hspR and/or hrcA. Said cells can be further subjected to one or more additional stress inducing stimuli in accordance with the present invention. Typical additional stress inducing stimuli include respiratory stress such as oxygen limitation, pH stress (for example acid stress at pH4) and metabolite restriction such as carbon or iron limitation.

The prokaryotic heat shock protein families DnaJ, DnaK, GroEL and GroES are encoded in operons, with the initial gene in the operon being a control gene which suppresses the expression of the heat shock protein genes contained within the operon. In *Streptomyces* and *Helicobacter* for example, expression of the hspR gene suppresses the expression of DnaJ and DnaK. Deletion of the hspR gene therefore results in a genetically modified microbe that constitutively expresses heat shock proteins (see Bucca et al. (2003) *Mol. Microbiol* 50(1)153-166). However, it should be noted that the two major heat shock protein families DnaK and GroEL are regulated by two different regulons hspR and hrcA. Of these heat shock regulons, the hsp70/DnaK regulon is under the control of hspR, while the hsp60/groEL regulon is under the control of hrcA. The deletion of both these genes would be required to maximally upregulate both Dnak and GroEL heat shock protein expression (Holmes et al. (2010) *Microbiology* 156:158-166 amd Aravindhan V. et al. (2009) FEMS Microbial Lett. 292 42-49). Homologous operons have been identified in a number of recently sequenced microbes, including other strains of *Streptomyces* and *Mycobacterium tuberculosis* and the commonly used related vaccine strain BCG.

Other repressor genes may also control the expression of other stress proteins and these may also be genetically modified to provide modified microbes that constitutively express stress proteins. These include, but are not limited to, the transcriptional control genes sigma and rho and the stress-gene regulatory protein genes hrcA, MerR and HmrR.

Accordingly, the present invention may further extend to the use of a genetically modified pathogen which has been genetically modified to knock out or disable at least one repressor gene which controls the expression of a heat shock protein, wherein said genetically modified pathogen is subjected to respiratory stress or acid stress prior to the isolation and/or purification of the induced heat shock protein complexes for use as the immunogenic determinants in vaccine compositions.

In certain embodiments, the cells are cells which have been genetically modified such that they express a heterologous protein which is derived from a cancerous cell. In alternative embodiments, the cells are cells which has been genetically modified such that they express a heterologous protein derived from a pathogen which causes an infectious disease in a host.

Infected Cells

In certain embodiments, the cells are host cells which are infected with a pathogenic organism. The complexes may be formed from a heat shock protein derived from the host cells complexed to a peptide fragment derived from the invading pathogen, or from a heat shock protein and peptide fragment which are both derived from the invading pathogen.

Accordingly, in certain embodiments the invention provides a method for the production of complexes formed between a heat shock protein and a peptide fragment, said method comprising, consisting of, or consisting essentially of the steps of:

culturing cells which are infected with a pathogen, exposing said cells to multiple stress inducing stimuli, and purifying the heat shock protein complexes from the cultured cells.

In certain embodiments, the multiple stress inducing stimuli comprises at least 2 stress inducing stimuli which are applied to the cells simultaneously and which can include heat stress and respiratory stress or heat stress and acid based stress.

The methods of the present invention advantageously provide a mixture of purified heat shock protein complexes wherein this mixture of heat shock protein complexes comprises different subtypes of heat shock proteins. That is, the heat shock protein components of the heat shock protein complexes may be heat shock proteins of different families of heat shock subtypes. For example, there may be a mixture of heat shock proteins derived from classes selected from, but not limited to, HSP60, HSP70 and/or HSP90, or from any other heat shock protein class which is present in a eukaryotic cell or a pathogenic cell. In certain embodiments, it is preferred that the heat shock protein complexes comprise or consist of heat shock proteins of the GroEL (the prokaryotic heat shock protein which is equivalent to HSP60 in mammalian cells) and/or DnaK (the prokaryotic heat shock protein which is equivalent to HSP70 in mammalian cells) heat shock protein families. Accordingly, in certain embodiments of the invention, the purification methods used herein are used to purify protein complexes wherein the heat shock protein component comprises DnaK and GroEL.

Inducing and Purifying Heat Shock Protein Complexes

In certain embodiments, the heat shock protein complexes are purified or isolated from a cell lysate obtained from the cell, e.g. the pathogenic cell, cancerous cell or the cell infected with a pathogen, which has been subjected to the stress-inducing stimuli.

Typically the stress protein complexes comprise heat shock proteins of different heat shock protein classes. In certain embodiments, the heat shock proteins are of the subtypes DnaK and/or GroEL. Said purified and/or isolated heat shock protein complexes, or a preparation or mixture comprising the same, can then typically be used as the immunogenic determinant in a vaccine composition to elicit an immune response and associated protective immunity against the pathogen or cancerous cell from which the stress protein complexes are derived, or against a pathogen which is infecting a cell from which the stress protein complexes are derived.

In certain embodiments, purifying the heat shock protein complexes comprises:

(i) providing a clarified cell lysate from the culture cells, wherein the cell lysate comprises the stress protein complexes, (ii) subjecting the cell lysate to purification using ion exchange, wherein the cell lysate is buffered to a pH within 2 units of the pI of the target heat shock protein complexes and wherein a salt gradient is used to elute the heat shock protein complexes, and (iii) obtaining an enriched preparation comprising the heat shock protein complexes.

In certain embodiments, the buffer comprises divalent cations which may be provided at a concentration of from about 0.1 mM to 100 mM. In certain embodiments, the divalent cation is a magnesium salt and/or a manganese salt. In certain embodiments, the buffer further comprises ADP (adenosine diphosphate) which may be provided at a concentration of from about 0.1 mM to 100 mM.

In certain embodiments the heat shock protein complexes comprise heat shock proteins of the classes DnaK and/or GroEL.

Vaccine Compositions

Typically, said purified heat shock protein complexes obtained by the foregoing aspect of the invention can be used as the immunogenic determinant in a vaccine composition for use in mediating an immune response against the pathogen from which the stress protein complexes were derived.

In various further aspects, the invention therefore extends to vaccine compositions, or to compositions which mediate or elicit an immune response, which comprise the heat shock protein complexes which are obtained by the methods of the invention. Said vaccine compositions are typically administered to mammals, in particular humans, in order to confer protective immunity against a pathogen. However, due to the acknowledged high level of homology between stress proteins from different species, vaccine compositions may be used to vaccinate a wide variety of animals.

As such, a further aspect of the invention provides a vaccine composition comprising, as the immunogenic determinant, purified heat shock protein complexes obtained by the method of the present invention.

In certain further aspects, the present invention provides a vaccine composition according to the invention, or a purified and/or isolated mixture of heat shock protein complexes obtained using the methods of the invention, for use in medicine.

In certain further aspects the present invention provides the use of heat shock protein complexes produced in accordance with any of the foregoing aspects of the invention in the preparation of a medicament for the prevention or treatment of an infectious disease or a cancerous or malignant condition.

In certain further aspects, the present invention provides heat shock protein complexes for use in a vaccine composition for the treatment or prevention of an infectious disease or a cancerous or a malignant condition.

In certain embodiments, the heat shock protein complexes or the vaccine compositions containing the same are administered as a prophylactic vaccine. In certain further embodiments, the purified stress protein complexes or the vaccine compositions comprising the same are administered as therapeutic vaccines.

In various further aspects, the present invention extends to the heat shock protein complexes or to preparations or mixtures comprising the same, or to vaccine compositions containing the same, for use as a booster vaccine to enhance the immune response generated in a host against a pathogen or cancer antigen to which the subject has previously been exposed to, typically by way of infection or due to the previous administration of a primary vaccine.

Compositions of the invention may be lyophilised or in aqueous form, solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses).

In various further aspects, the present invention provides a method for producing a vaccine composition comprising the step of mixing the purified heat shock protein complexes of the invention, or a preparation or mixture comprising the same, together with at least one pharmaceutically acceptable excipient, carrier or diluent.

In one embodiment of the present invention there is provided a vaccine composition for use in a medicament for the treatment or prevention of a pathogenic disease, such as that caused by infection by a pathogenic bacteria selected from the group comprising, but not limited to, *Bordetella pertussis, Clostridium tetani, Clostridium difficile, Corynebacterium diphtheriae, Haemophilus influenzae b, Mycobacterium tuberculosis* and *Mycobacterium leprae, Salmonella typhi, Streptococcus pneumonia, Vibrio Cholerae* and *Neisseria meningitides*. In a further embodiment of the present invention there is provided a vaccine composition for use in a medicament for the treatment or prevention of a pathogenic disease, such as that caused by infection by a pathogenic or oncogenic virus selected from the group comprising, but not limited to, influenza, hepatitis, herpes, human immunodeficiency virus (HIV), human papaloma virus (HPV), respiratory synctial virus (RSV), Polyoma, cytomegalovirus (CMV), Epstein-Bar virus (EBV), Rotovirus, Norovirus, coronavirus, hepatitis A virus (HAV), hepatitis B (HBV), hepatitis C (HCV), human papillomavirus (HPV), Kaposi's Sarcoma-Associated Herpesvirus (KSHV), Herpes Simplex virus (HSV), Respiratory Syncytial Virus, Ebola virus, Marburg virus, West Nile virus (WNV), St Louis Encephalitis virus (SLEV), Rift Valley Fever virus (RVFV), Influenza viruses, coronaviruses, rhinovirus, adenovirus, SIV, rotavirus, arbovirus, measles virus, polio virus, rubella virus, mumps virus, papova virus, varicella-zoster virus, varicella virus, huntavirus and cytomegalovirus.

In a yet further embodiment of the present invention there is provided a vaccine composition for use in a medicament for the treatment or prevention of cancer and neoplastic disease.

Additionally, a yet further aspect of the invention extends to a method of immunising a subject, typically a human, against disease caused by *Bordetella pertussis, Clostridium tetani, Clostridium difficile, Corynebacterium diphtheriae, Haemophilus influenzae* type b, *Mycobacterium tuberculosis* and *leprae, Salmonella typhi, Vibrio Cholerae, Streptococcus pneumonia, Neisseria meningitidis* and pathogenic and oncogenic viruses, which method comprises administering to the host an immunoprotective dose of the vaccine of the invention.

The amount of antigen (i.e. the immunogenic determinant) in each vaccine dose is selected as an amount which induces an immunoprotective response in the vaccinated subject without significant adverse side effects. The amount of antigen will vary depending upon which specific immunogen is employed and how it is presented. However, it will be understood that the enhanced immune response mediated against the purified complexes of the invention will mean that an enhanced immune response will be mediated against complexes produced using the present methodology, when compared to a vaccine composition comprising a similar amount of protein complexes obtained using the production methods known in the art.

The invention further provides for the use of the heat shock protein complexes of the invention in a method of vaccinating a subject to induce immunity against a pathogen derived infectious disease or cancerous or malignant condition.

Accordingly a yet further aspect of the invention provides for a method of vaccinating a subject against a pathogen derived infectious disease or a cancerous condition, said method comprising the steps of:

providing a vaccine composition comprising, as the immunogenic determinant, a heat shock protein complex provided according to any one of the methods of the present invention, said heat shock protein complex being derived from a cancerous cell, a pathogenic cell or a cell infected with a pathogen or expressing a heterologous antigen which has been subjected to heat shock and respiratory or acid based stress inducing stimuli against which protective immunity is desired, and comprising different heat shock protein types as a mixture, and administering the vaccine composition comprising the heat shock protein complex to the subject in a therapeutically effective or prophylactically effective amount sufficient to elicit an immune response in the subject against the heat shock protein complex.

As used herein, the term "vaccine composition" means any, composition containing an immunogenic determinant which stimulates the immune system in a manner such that it can better respond to subsequent challenges, pathogenic infections or oncogenesis. It will be appreciated that a vaccine usually contains an immunogenic determinant and optionally an adjuvant, the adjuvant serving to non-specifically enhance the immune response to the immunogenic determinant.

In certain embodiments, the subject is an animal, typically a human. The methods of the invention can also be used to purify stress protein complexes for use in a vaccine composition for the treatment of other animals such as horses, cattle, goats, sheep, swine and birds.

In certain embodiments, the microbial pathogen from which the induced heat shock protein complexes of the invention are derived can be selected on the grounds that it causes disease or infection. The vaccine compositions provided by the invention may be used either prophylactically or therapeutically. The inventors, however, recognise that the compositions may be particularly useful as prophylactic vaccines due to their economy of production and their ability to elicit a protective immune response against the pathogen from which the peptide or the peptide and heat shock protein is derived.

The inventors have further surprisingly identified that heat shock protein complexes which are obtained using the methods of the invention can be used as "booster" vaccinations, said booster vaccinations enhancing the immunity provided in a subject against a pathogen or a cancerous condition, wherein the initial immunity was conferred by vaccination with a live or attenuated vaccine, or by a vaccine composition wherein the immunogenic determinant was a stress protein-peptide complex.

Accordingly, a yet further aspect of the invention provides for a method of boosting a protective immune response in a subject against a pathogen derived infectious disease or a cancerous condition, wherein said protective immune response has been elicited by the previous administration of a live or attenuated vaccine or of a stress protein complex comprising a peptide derived from the pathogen against which immunity is desired, said method comprising the steps of:

providing a composition comprising a heat shock protein complex or complexes prepared according to any foregoing method of the present invention, said purified heat shock protein complex or complexes being derived from a cancerous cell, a pathogen infected cell or a pathogen against which protective immunity is desired and comprising different stress protein types as a mixture, and administering the composition to the subject in an amount sufficient to elicit an immune response in the subject against the stress protein complex or complexes.

In certain further embodiments, the heat shock protein complex containing vaccines of the present invention may be used for boosting immune responses in animals that have been previously immunised with other subunit, multi-subunit, carbohydrate or conjugate vaccines. In yet further embodiments, the heat shock protein complex vaccines of the present invention can be used to boost the immune responses against a target antigen in animals that have been previously immunised with nucleic acid or live vaccines. In yet further embodiments, the heat shock protein complex containing vaccine compositions of the present invention provide for boosting immune responses mediated in subjects that have been previously immunised against a pathogen or cancer specific antigen.

In certain further aspects, the present invention extends to vaccine compositions comprising the heat shock protein complexes induced by the methods of the present invention for use in boosting immune responses in animals, wherein the animal has previously been vaccinated with a vaccine composition comprising at least one pathogen derived antigen, a pathogen, in particular an attenuated pathogen, or a cancer specific antigen.

In certain further aspects, the present invention extends to vaccine compositions comprising the heat shock protein complexes produced by the invention for use in boosting immune responses in animals, wherein the animal has previously been exposed to a pathogen or cancer antigens derived from the same or related cells as those from which the heat shock protein complexes have been derived.

In certain further embodiments, the present invention provides compositions for the preparation of cellular vaccines such as dendritic cells (DCs) which have been pulsed with the purified stress protein complexes of the invention. Administration of such pulsed dendritic cells to a subject will result in a T-cell mediated response being directed against the heat shock protein complexes. Such a therapy can be particularly effective when treating a subject with a cancerous or malignant condition. In such embodiments, typically the heat shock protein complexes are derived from a cancerous cell.

In certain embodiments, the vaccine composition of the invention may be replaced with a composition for inducing an immune response, or by a composition for eliciting an immune response, said compositions typically comprising the same immunogenic determinants as those provided in the vaccine compositions described herein.

DETAILED DESCRIPTION OF THE INVENTION

Figure 1A:
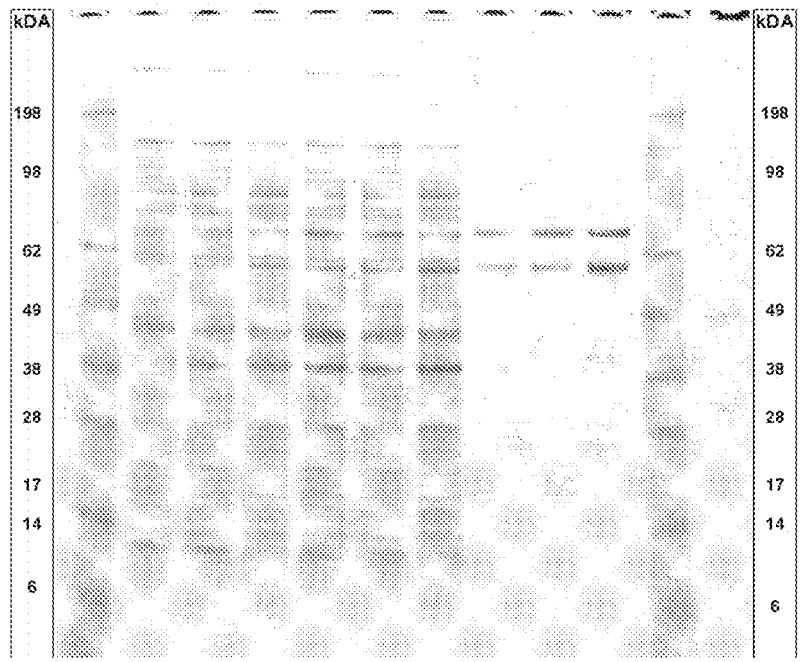
FIG. 1A shows the time course of heat shock protein induction from cells which are stressed with both heat shock and oxygen limitation (respiratory stress). Lane 2 shows pre-induction protein levels and lanes 3-7 show 30 minute intervals of a 0-2 hour stress induction. Increasing amounts of protein (GroEL and DnaK) can be seen in the bands at 60 and 70 KD in lanes 3 to 7, these representing increased amounts of GroEL (70 kDa) and DnaK (60 kDa). Lanes 8 and 9 show increasing amounts of hsp60 and hsp70 standards, with these being the major heat shock proteins induced. Lanes 1 and 11 contain molecular weight (MW) markers.

The present invention provides stress protein-peptide complexes, wherein the production of the stress protein is induced following the cell being subjected to a plurality of stress inducing stimuli, typically a heat shock and a respiratory stress or a heat shock and an acid based stress.

The inventors have identified that stressing a cell with at least two stress inducing stimuli results in a significantly higher level of heat shock proteins being induced, with this increase in production being assessed by the inventors as comprising at least a two-fold increase, preferably three- or four-fold, over protein levels produced following exposure to a single stress inducing stimulus. This is particularly surprising for disparate stress inducing stimuli such as heat and respiratory stress as these are generally thought to be subject to control by different genetic and transcriptional elements. Accordingly, it is entirely unexpected that following the exposure of a prokaryotic cell to heat stress, the amount of heat shock protein produced in response to that stress inducing stimulus can be further (and significantly) enhanced by exposing the cell to a secondary stress inducing stimulus.

Furthermore, the inventors have surprisingly identified that heat shock protein complexes which are produced using the methods of the invention are more immunogenic than similar complexes obtained following a single stress inducing stimulus, or when compared to heat shock protein complexes which are constitutively produced. Hence, the heat shock protein complexes produced by the methods of the invention are more immunogenic than those produced using standard production methods known in the art and can be used to produce improved vaccine preparations.

Heat Shock Protein Complexes

In certain embodiments, the heat shock protein complex can be a heat shock protein complex (HspC) comprising a heat shock protein which is complexed to a peptide or peptide fragment. In certain embodiments, the heat shock protein can be any suitable heat shock protein which is derived from the cell lysate which is to be purified. In certain embodiments, the heat shock protein may be selected from any one of the families of the group comprising, but not limited to, hsp20-30 kD; hsp40; hsp60; hsp70; hsp90; and hsp100. In certain further embodiments, the stress protein may be a protein which is classed as a chaperone protein. Such a protein may include, but is not limited to proteins selected from the group consisting of: DnaK, DnaJ, GroEL, GroES, hspX, acr2, AAA+, clpA/B, HtpG, TRIC, CCT, IbpA, IbpB, calrecticulin, hsp40, hsp70, hsp72, hsp90, grp94, grp75, BiP/grp78, grp75/mt, gp96 and small heat shock proteins (hsps). In certain embodiments, it is preferred that the heat shock protein is GroEL and/or DnaK.

In certain embodiments, where a mixture of complexes is provided, this may comprise heat shock proteins of one particular family, for example, the hsp70 or hsp60 families, although it is preferred that the mixture comprises different heat shock protein complexes derived from different families. The method of the present invention provides a method for the purification of all complexes comprising a heat shock protein complexed to a (antigenic) peptide, irrespective of the identity, molecular weight or size of the peptide.

In certain embodiments, the target heat shock protein complex comprises a heat shock protein complex derived from a host cell which has been genetically modified to constitutively express stress protein genes, and/or express a heterologous protein, such as an antigenic peptide or peptide fragment. In certain further embodiments, the cell may be a host cell expressing a heterologous gene, for example a yeast cell carrying an expression vector construct comprising an antigenic gene of interest. In yet further embodiments, the cell may be a cancerous cell derived from a human or animal subject.

In certain further embodiments, heat shock protein complex (HspC) enriched preparations (HEPs) comprise heat shock proteins from different stress protein families or classes, such as DnaK, GroEL, hsp60, hsp65, hsp70 and hsp90, said families being co-purified as a mixture using the methods of the invention.

In certain further embodiments, the heat shock protein complex (HspC) enriched preparations (HEPs) may be heat shock protein complexes of a particular molecular weight. In certain embodiments, the stress protein complexes have a molecular weight in the range of 50 KDa to 900 KDa.

Administration of Vaccine Compositions

In certain embodiments, the vaccine compositions of the invention may further comprise at least one adjuvant. In certain embodiments, the adjuvant is selected from the group consisting of, but not limited to, Freund's complete adjuvant, Freund's incomplete adjuvant, Quil A, Detox, ISCOMs and squalene. Further suitable adjuvants include mineral gels or an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-0-deacylated MPL, quit A, Saponin, QS21, Freund's Incomplete Adjuvant (Difco Laboratories, Detroit, Mich.), Merck Adjuvant 65 (Merck and Company, Inc., USA), AS-2, AS01, AS03, AS04, AS15 (GSK, USA), MF59 (Chiron, Sienna, Italy), CpG oligonucleotides, bioadhesives and mucoadhesives, microparticles, liposomes, outer membrane vesicles, polyoxyethylene ether formulations, polyoxyethylene ester formulations, muramyl peptides or imidazoquinolone compounds.

The vaccine compositions or stress protein complexes of the present invention may be administered to a subject in need of treatment via any suitable route. Typically the composition is administered parenterally. Examples of other possible routes for parenteral administration include, but are not limited to, intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal or rectal. The formulation may be a liquid, for example, a physiologic salt solution containing non-phosphate buffer at pH 6.8-7.6, or a lyophilised or freeze dried powder.

In certain embodiments, the composition is deliverable as an injectable composition. For intravenous injection, the stress protein complexes will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or Lactated Ringer's injection. Preservatives, stabilisers, buffers, antioxidants and/or other additives may be included, as required.

In certain embodiments, the injection method can be needleless or may use a needle which penetrates the dermis. In certain further embodiments the vaccine is suitable for oral administration, or can be administered transdermally, or by pulmonary delivery. In certain embodiments, the vaccine composition is administered as a prophylactic vaccine. In certain embodiments, the vaccine composition is administered as a therapeutic vaccine. In yet further embodiments the vaccine composition is administered as a booster vaccine to any previously administered vaccine mediated by a primary immunisation schedule.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The vaccine compositions or heat shock protein complexes of the present invention may also be administered via microspheres, liposomes, other microparticulate delivery systems or sustained release formulations placed in certain tissues including blood.

Dosage regimens can include a single administration of the composition of the invention, or multiple administrative doses of the composition. The compositions can further be administered sequentially or separately with other therapeutics and medicaments which are used for the treatment of the condition for which the composition of the present invention is being administered to treat.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Definitions As herein defined, the term "stress inducing stimulus" means a stimulus which is capable of inducing a stress response within a cell or cells subjected to the stimulus. As herein defined, the term "plurality of stress inducing stimuli" or "multiple stress inducing stimuli" refers to at least two stress inducing stimuli and means two, three or more stress inducing stimuli. The stress inducing stimulus may include, but is not limited to, respiratory stress, cultivation under limited nutrient levels, exposure to a cytokine (such as tumour necrosis factor (TNF) or interferon gamma (IFN-gamma)), osmotic shock of a pathogen (in particular, once it has been cultivated to statutory growth phase by the addition of high concentrations of an electrolyte, such as sodium chloride, to the cultivation medium), acid based stress, pH variation, metabolite restriction or nutrient starvation, such as iron or carbon limitation, cultivation under high pressure, exposure to heavy metals and exposure to oxidising agents.

Unless otherwise defined, all technical and scientific terms used herein have the meaning commonly understood by a person who is skilled in the art in the field of the present invention.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

As used herein, the term "treatment" and associated terms such as "treat" and "treating" mean the eliciting of protective immune response against an immunogenic determinant in order to confer long term protective immunity against the pathogen or cancer cell from which the immunogenic determinant of the vaccine composition is derived. The term 'treatment' therefore refers to any regimen that can benefit a subject. The treatment may be in respect of an existing condition or may be prophylactic (preventative treatment). Treatment may include curative, alleviative or prophylactic effects.

As used herein, the term "therapeutically effective amount" means the amount of a stress protein complex or vaccine composition of the invention which is required to induce a protective immune response against an infectious disease or cancerous condition. As used herein, the term "prophylactically effective amount" relates to the amount of a multiple stress protein complex or vaccine composition which is required to prevent the initial onset, progression or recurrence of an infectious disease or cancerous condition. The term "therapeutic" does not necessarily imply that a subject is treated until total recovery. Similarly, "prophylactic" does not necessarily mean that the subject will not eventually contract a disease condition.

A "subject" in the context of the present invention includes and encompasses mammals such as humans, primates and livestock animals (e. g. sheep, pigs, cattle, horses, donkeys); laboratory test animals such as mice, rabbits, rats and guinea pigs; and companion animals such as dogs and cats. It is preferred for the purposes of the present invention that the mammal is a human. The term "subject" is interchangeable with the term "patient" as used herein.

As used herein, the terms "mount", "mounted", "elicit" or "elicited" when used in relation to an immune response mean an immune response which is raised against the immunogenic determinant of a vaccine composition which is administered to a subject. Typically the immunogenic determinant of the vaccine composition comprises the isolated and/or purified stress protein complexes obtained using the methods of the present invention.

As used herein, the term "immune response" includes T cell mediated and/or B cell mediated immune responses that are influenced by modulation of T cell co-stimulation. The term immune response further includes immune responses that are indirectly effected by T cell activation such as antibody production (humoral responses) and the activation of cytokine responsive cells such as macrophages.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. Reference to any prior art in this specification is not, and should not be taken as, an acknowledgment or any form of suggestion that this prior art forms part of the common general knowledge in any country.

EXAMPLES

The present invention will now be described with reference to the following examples which are provided for the purpose of illustration and are not intended to be construed as being limiting on the present invention.

Example 1—Improved Induction and Immunogenicity of Stress Proteins in Gram Negative Organisms by Multiple Stress Stimuli

*Neisserial* strains (*N. lactamica* and MC58) were initially grown in 500 mL non-baffled Erlenmeyer flasks containing 100 mL Frantz medium at 37° C. with shaking at 180 rpm for 12 hours and then inoculated into a 60 L fermenter containing 54 L Frantz medium supplemented with essential amino acids. The culture was grown at 37° C. with dissolved oxygen tension (DOT) maintained at >30% by agitation cascade to a maximum of 500 rpm. DOT was measured using a galvanic dissolved oxygen probe (New Brunswick Scientific) or a redox sensor (Mettler Toledo). Final fermentation cultures were heat stressed by raising the temperature of the fermenter to 44° C. at a rate of 0.25-0.5° C./min. In some cultures, an additional stress to heat shock was applied by oxygen limitation (respiratory stress). This was achieved by removing the dissolved oxygen tension (DOT) cascade control as the temperature of the culture rose towards 44° C. and manually reducing the agitation rate to approximately 320-350 rpm. Samples for product analysis were removed at pre, 0, 1 and 2 hours post stressing and induction of heat shock proteins analysed by SDS-PAGE analysis and western blotting using standard equipment and protocols (Invitrogen).

Figure 1B:
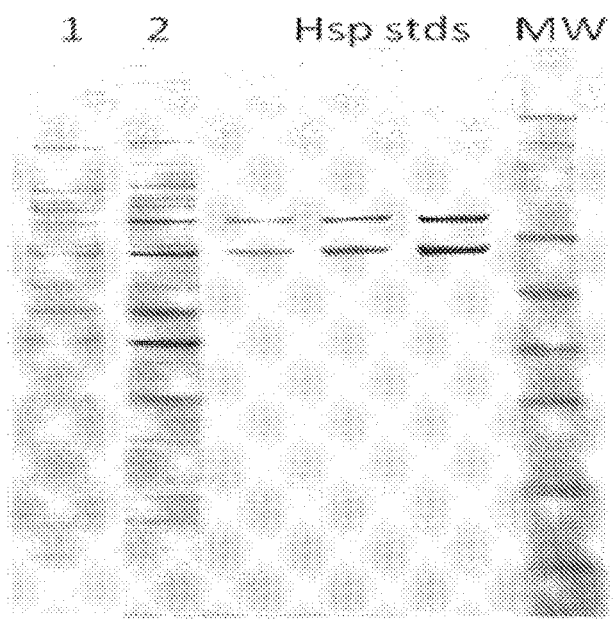
FIG. 1B shows a comparison of heat shock protein production following heat shock alone (lane 1) and heat shock and respiratory stress (oxygen limitation) (lane 2). Lane MW shows molecular weight markers and the lanes marked "Hsp stds" shows purified hsp60 and hsp70 proteins. A comparison of lanes 1 and 2 shows that there is a significantly higher level of heat shock protein induction in lane 2, this being depicted by the presence of significantly darker bands, corresponding to the bands seen in the hsp60 and hsp70 marker lanes (Hsp stds), FIG. 2 (A-F) shows the immune response to heat shock protein complexes made from cells subjected to heat shock only (groups 1 and 2) and to a combination of heat shock and respiratory stress (group 3) as assayed by antibody-dependent opsonophagocytosis (OPA) of fluorescently labelled clinically relevant *Neisserial* strains (panels A-F). The positive control (column 1) shows results using sera from animals vaccinated with an outer membrane vesicle (OMV) preparation from the homologous strain. Group 1 shows results using sera from animals vaccinated with complexes produced using heat stress inducing stimulus only, purified by Ion-exchange using a HEPES based buffer. Group 2 shows results using sera from animals vaccinated with complexes produced using heat stress inducing stimulus only, purified by Ion-exchange using a Tris based buffer. Group 3 shows results using sera from animals vaccinated with complexes produced using a combination of heat shock and respiratory stress stimuli, using the same Tris buffer purification as used in Group 2.

Typical results obtained are shown in FIG. 1, which clearly shows the time dependent induction of GroEL and DnaK by the use of respiratory stress as a supplement to heat stress (FIG. 1A, lanes 2-7) as can be identified by co-migration with recombinant standards (FIG. 1A, lanes 8-10) and confirmed by western blotting. The unexpectedly additive effects of disparate stress stimuli is clearly demonstrated by a direct comparison (FIG. 1B) of cultures subjected to only heat shock (lane 1) and a combination of heat and respiratory stress (lane 2) which shows a clear enhancement of the major heat shock protein families hsp60 and hsp70.

Figure 2:
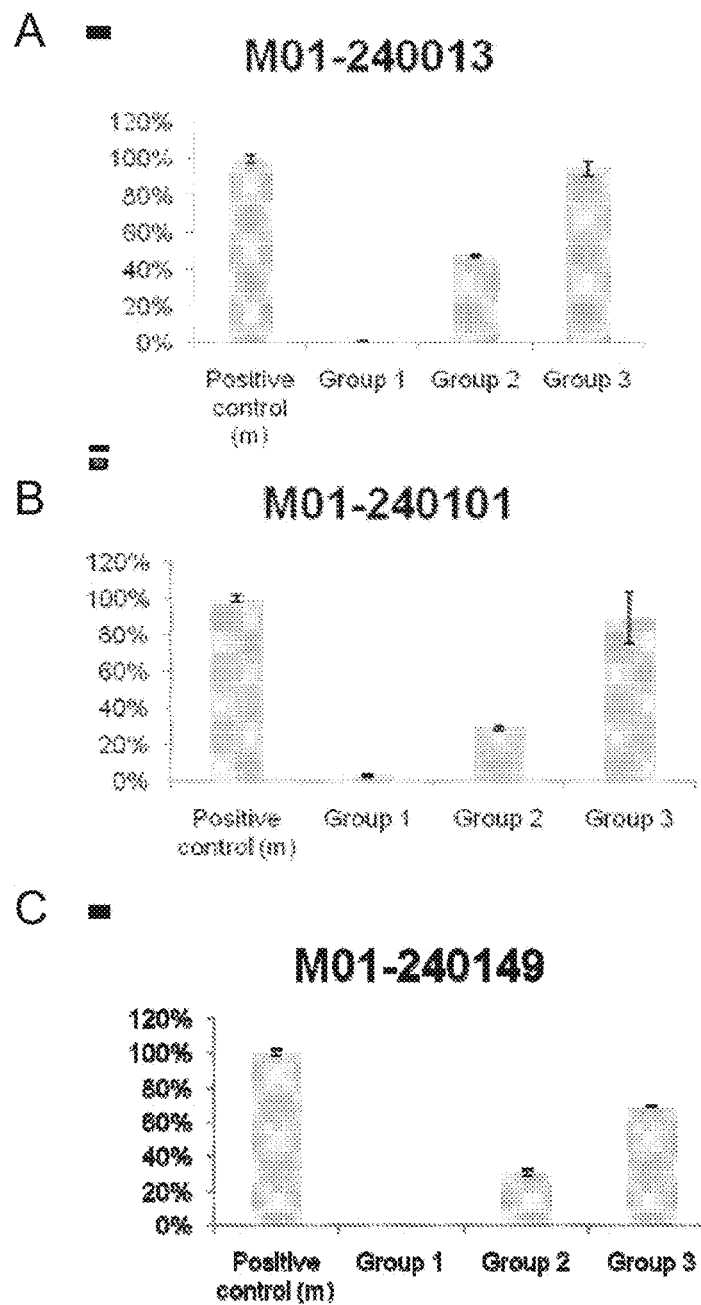
Figure 2:
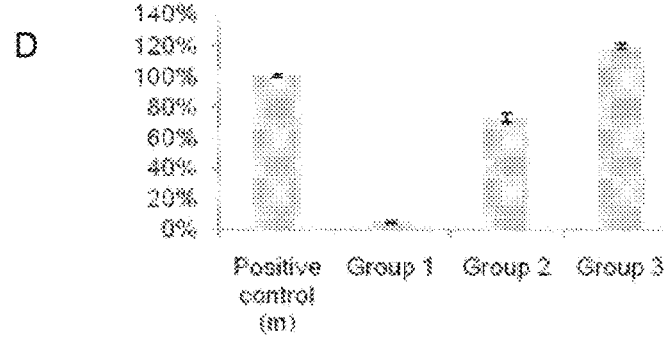
Figure 2:
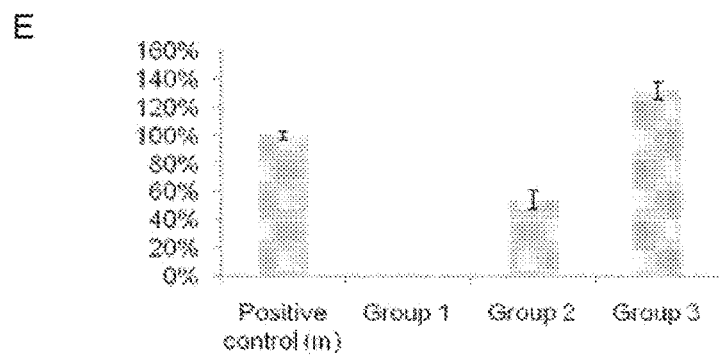
Figure 2:
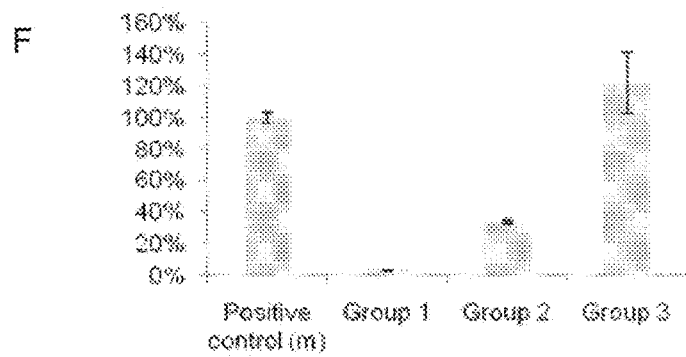
Figure 3A:
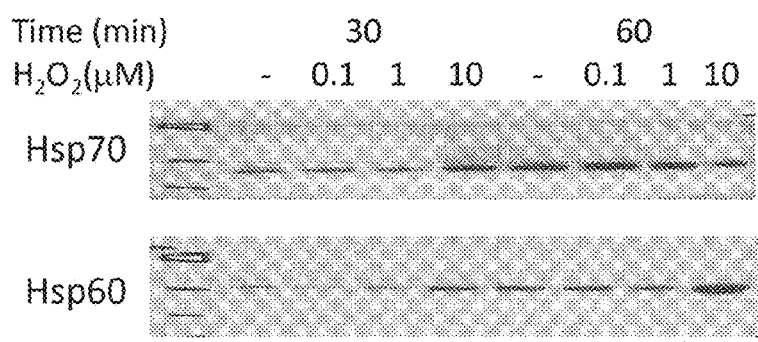
FIG. 3 (A-B) shows the time course of stress protein induction from *S. pneumoniae* cells which are stressed with a number of distinct stress stimuli, namely oxidative, osmotic, heavy metal and acid stress. Increasing amounts of heat shock proteins (hsp60 and hsp70) can be seen in the Western blots using antibodies against GroEL and DnaK to analyse stress inducing stimuli for use in combination with heat shock or a combination of heat and respiratory stress.
Figure 3A:
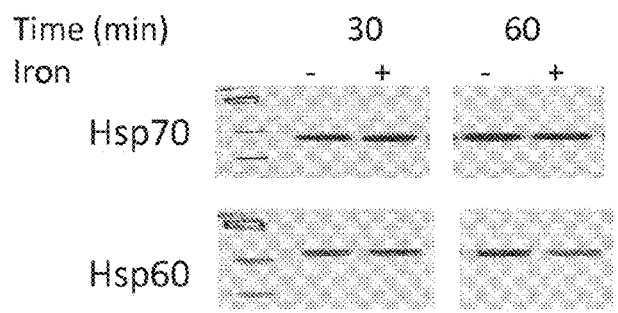
Figure 3B:
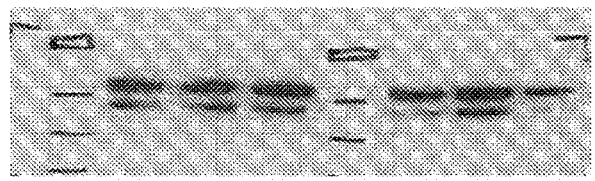
Figure 3B:
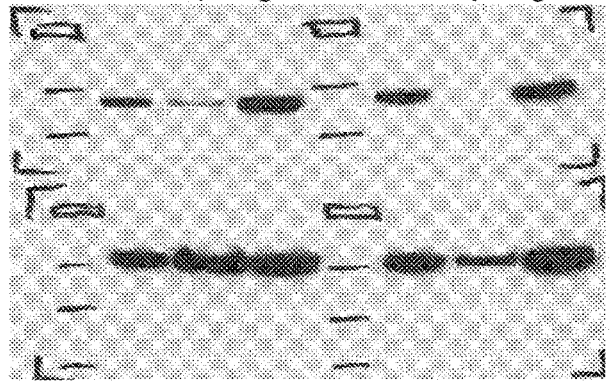
Figure 4:
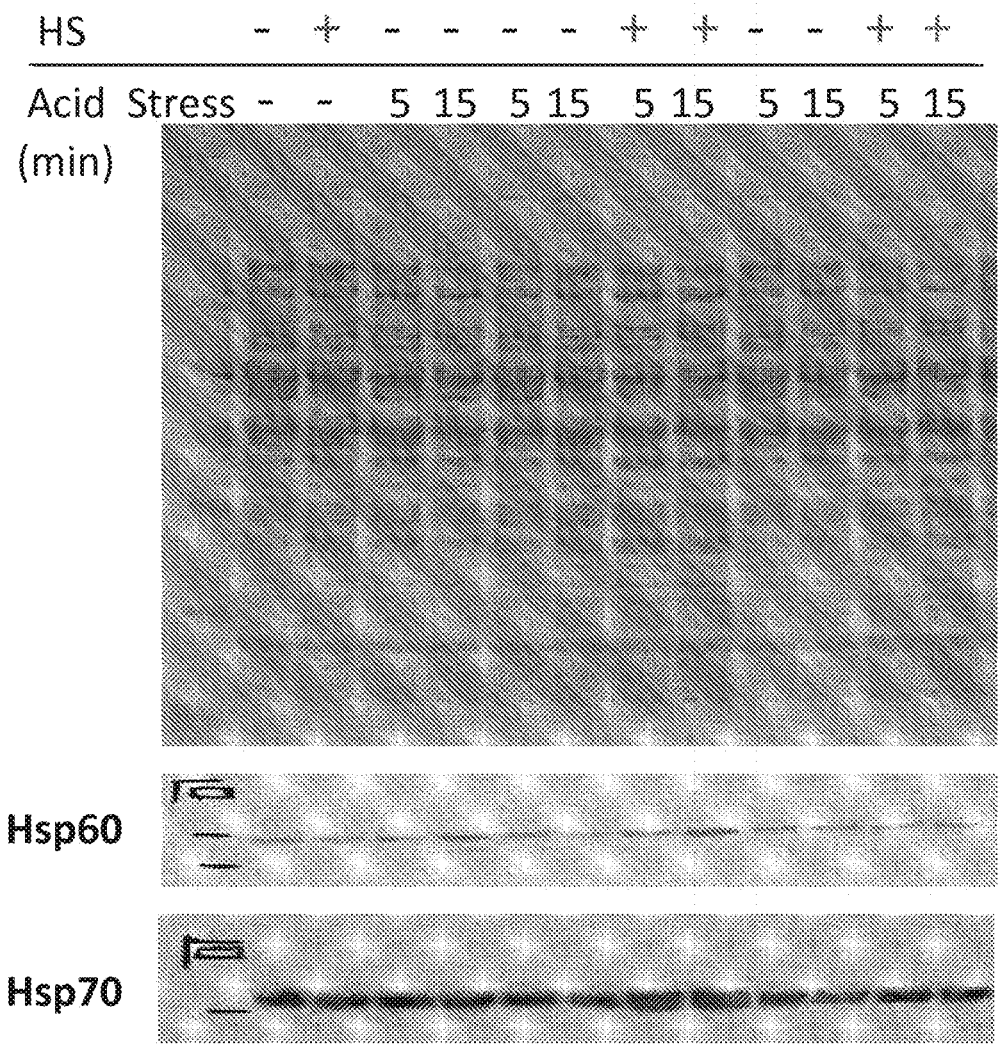
FIG. 4 shows the induction of stress proteins from *S. pneumoniae* cells which are stressed for either 5 or 15 minutes with a combination of heat and acid stress. Heat shock was constant at 42° C. and acid shock was at pH 4.5, 5 and 5.5. The optimal combination of heat shock and pH 5 can be determined from a comparison of the Western blots using antibodies against hsp60 and hsp70 in lanes 7 and 8, which show a clear improved induction of both GroEL and DnaK as compared to lanes 1 to 4 which show cells subjected to only a single stress inducing stimulus.
Figure 5:
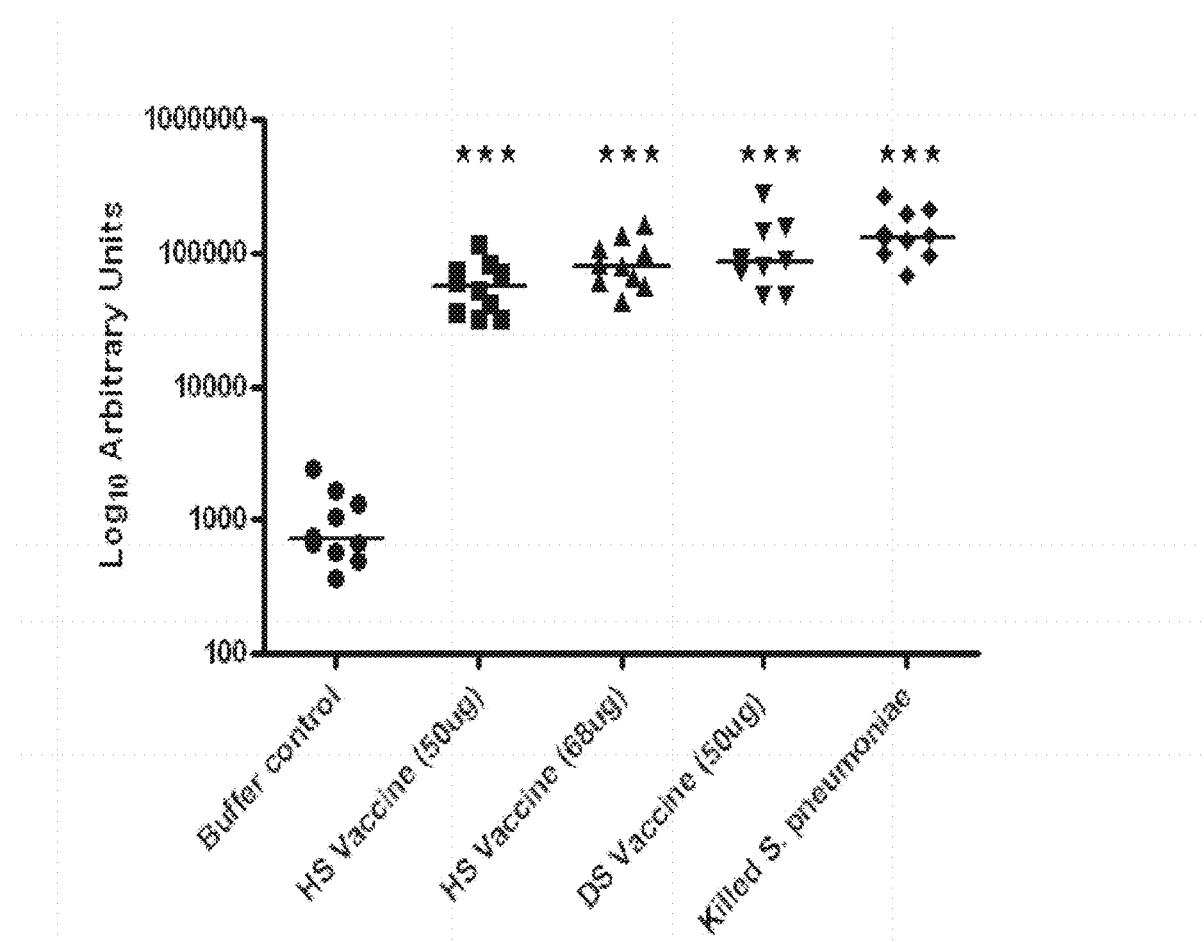
FIG. 5 shows the immune response to stress protein complexes made from cells subject to either heat stress alone (HS vaccine) or a double stress combination of heat and acid stress (DS vaccine), as assayed by antibody-dependent opsonophagocytosis assay (OPA) of fluorescently labelled *S. pneumoniae* strain Rx1. The positive control is sera from mice immunised with whole killed cells from the homologous strain (Rx1) and the isolated stress protein complexes from the single stress (heat shock only) were additionally tested at a higher dose (68 μg) than the double stress vaccine (50 μg).
Figure 6:
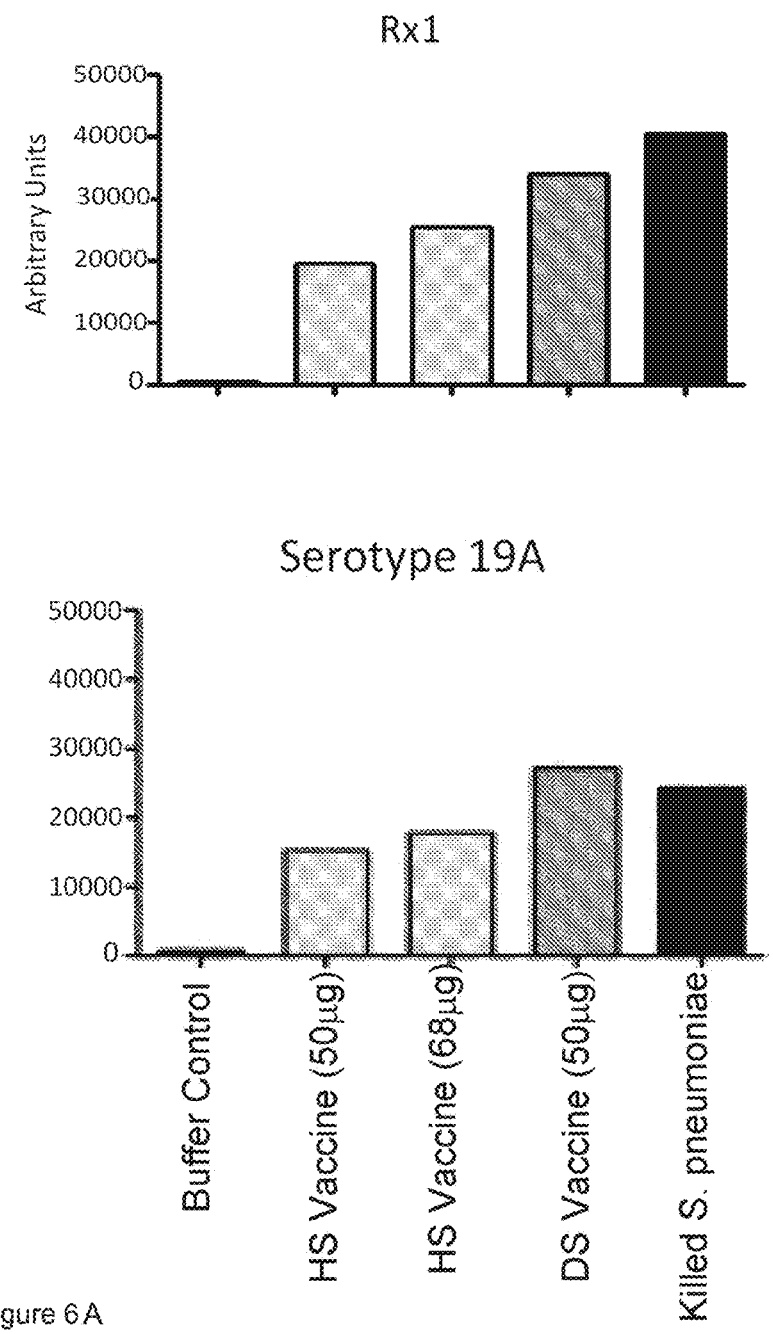
FIG. 6 shows the breadth of the immune response to stress protein complexes made from cells subject to either heat stress alone (HS vaccine) or a double stress combination of heat and acid (DS vaccine), as assayed by enzyme-linked immunoassay (ELISA) against clinically relevant *S. pneumoniae* strains of different, heterlogous, serotypes. The positive control is sera from mice immunised with whole killed cells from the strain Rx1 and the stress protein complexes from the single stress (heat shock only) were additionally tested at a higher dose (68 μg) than the double stress vaccine (50 μg).
Figure 6B:
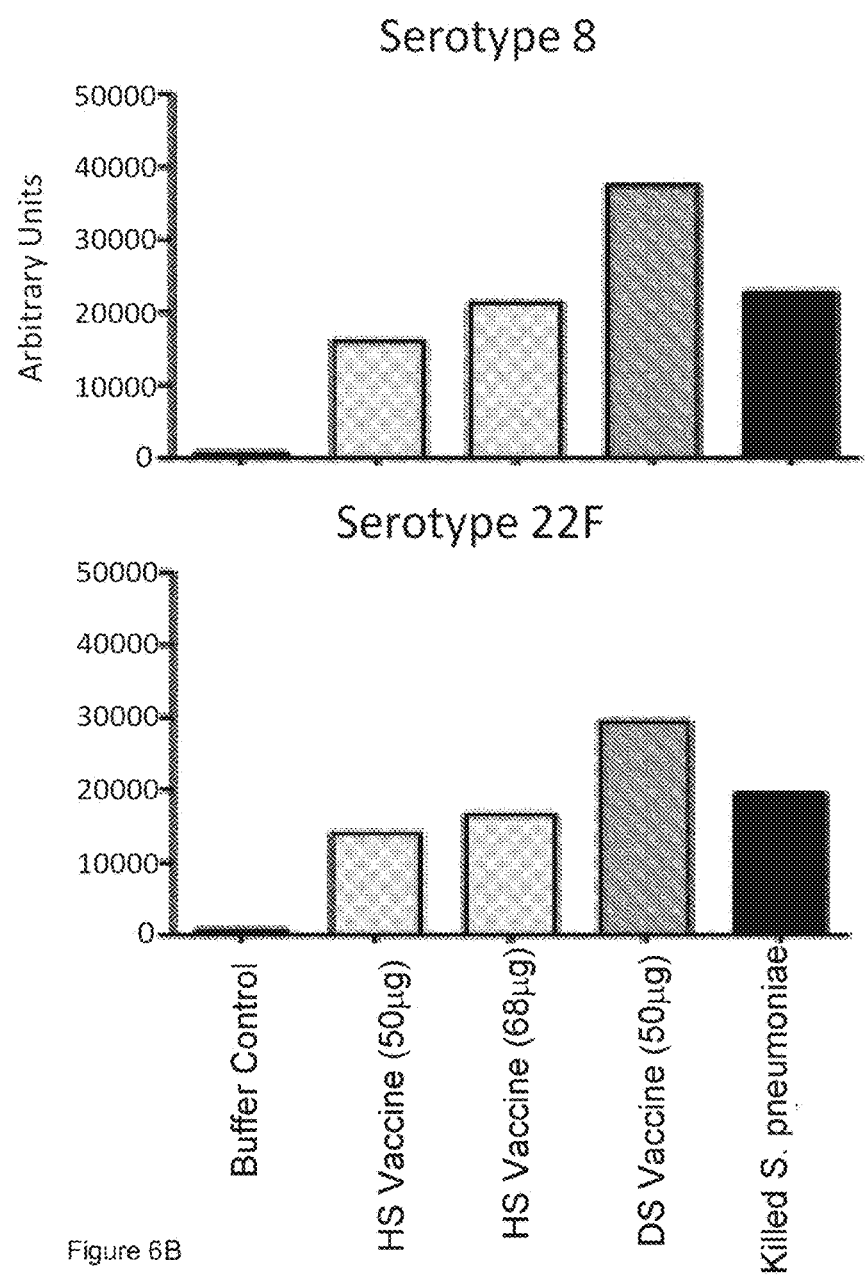

The stressed cell pellets were also resuspended in PBS, lysed using an Emulsiflex C5 homogeniser and used to prepare heat-shock protein complex. (HspC) enriched vaccine compositions by Ion exchange chromatography as described in PCT Patent Application No. WO 2010/026432. The vaccines were used to immunise groups of 8 mice and the antibody responses quantified for functionality using complement binding and opsonophagocytosis assays as described in WO 2010/026432. Typical results obtained are shown in FIG. 2 which clearly show improved immune responses elicited by vaccine compositions comprising, as an immunogenic determinant, heat shock protein complexes derived from cultures that had been subjected to both heat and respiratory stress (group 3), as compared to vaccine compositions comprising, as an immunogenic determinant, heat shock protein complexes derived from cultures that had been subjected to heat shock alone (group 2), as assayed by opsonophagocytosis (FIG. 2). The cross-reactive immunogenicity induced was assayed against a number of fluorescently labelled heterologous $Neisserial$ strains and normalised to a homologous OMV vaccine as the positive control. The improved cross-reactive immunogenicity elicited against a number of clinically relevant $Neisserial$ strains, M01-240013, M01-240101, M01-240149, M01-240185 and M01-240355 and H44/76-SL, covering a broad spectrum of heterologous circulating serotypes, is illustrated in FIG. 2A-F.

Example 2—Improved Induction and Immunogenicity of Stress Proteins in Gram Positive Organisms by Multiple Stress Stimuli The Mycobacterial vaccine strain, BCG Danish (Statens Serum Institute) was grown in a Sauton media supplanted with 0.1% Tween 80 and antifoam emulsion C (Sigma). Fermentation was carried out in a 3 L bioreactor (Braun) using 2l cultures grown at 37° C. with shaking at 360 rpm with dissolved oxygen tension (DOT) maintained at >20% by agitation cascade to a maximum of 500 rpm. Final fermentation cultures were heat stressed (heat shocked) by raising the temperature of the fermenter to 44° C. at a rate of 0.25-0.5° C./min for 1 hr. In some cultures oxygen limitation (oxidative stress) was achieved by removing the dissolved oxygen tension (DOT) cascade control as the temperature of the culture rose towards 44° C. and manually reducing the agitation rate to approximately 320-350 rpm.

The results obtained showed a clear additive induction of the major heat shock proteins GroEL and DnaK by the use of respiratory stress in addition to heat stress. Heat-shock protein enriched vaccine compositions were prepared by ion exchange chromatography as described in WO 2010/026432 and to immunise groups of mice and rabbits. The antibody responses again showed improved immune responses elicited by vaccine compositions wherein the immunogenic determinant comprises heat shock protein complexes derived from cultures that had been subjected to both heat and respiratory stress, as assayed by western blotting and ELISA using serum from the immunised animals. The improved immunogenicity resulted in an increased protection against aerosol challenge with live H37Rv, with a further 0.8 log reduction in lung colony forming units in mice immunised with vaccine compositions from the double stressed compared to single stressed BCG.

Example 3—Improved Induction and Immunogenicity of Stress Proteins in Facultative Anaerobes by Multiple Stress Stimuli Laboratory strain Rx1 of *Streptococcus pneumoniae* was grown in Hoeprich Medium, pH 7.5 at 37° C. in a shaking incubator in an atmosphere of 5% $CO_2$. Cultures were seeded using 0.5 ml of a master stock (OD 0.3) into 40 ml media and grown at 50 rpm for 5-6 hours (OD 0.2). Cultures were then subjected to multiple stress inducing stimuli, including heat shock at 40° C. for 30-60 minutes, respiratory shock by removal of the $CO_2$ source, pH stress by addition of HCl to adjust culture to pH 5 and iron restriction. Samples of the cultures were analysed for the induction of heat shock proteins by SDS-PAGE analysis and Western blotting using standard equipment and protocols (Invitrogen). Comparisons of the induction of GroEL (hsp60) and DnaK (hsp70) by the various stress stimuli (FIG. 3) were used to select the most promising combinations. FIG. 4 shows the results obtained using the selected combination of heat shock and acid stress (lanes 8,9 and 12,13) which showed a clear improvement in the induction of both GroEL and DnaK over the induction by either heat shock (lane 3) or acid stress (lanes 4-6) alone.

Heat-shock protein enriched vaccine compositions (HEPs) were prepared from the Rx1 cultures subjected to heat shock or a double stress combination of heat and acid stress using ion exchange chromatography as described in WO 2010/026432 and used to immunise groups of mice. The antibody responses elicited showed clearly improved immune responses mediated by vaccine compositions from multiple stimuli as assayed by western blotting, ELISA (FIG. 5) and OPA (FIG. 6) using serum from the immunised animals.

HEPs were isolated from *S. pneumoniae* subjected to either just heat shock at 42° C. or a double stress combination of heat and acid shock (pH5) and used to immunise mice. The HEP vaccine from the single stress was also used at a higher dose (68 μg and 50 μg) than the vaccine from the double stress (50 μg) and compared to a vaccine of whole killed pathogen as a positive control. The HEP vaccines from the *S. pneumoniae* cells induced by the double stress (DS vaccine) show clearly improved immunogenicity over the single stress vaccine (HS vaccine) even when the latter is used at a significantly higher dosage (FIGS. 5 & 6). This improved immunogenicity is seen not just in the affinity and avidity of the antibodies elicited as assessed by the OPA assay (FIG. 5), but also in the cross-reactive breadth of the antibodies produced as assessed by ELISA against clinically relevant *S. pneumoniae* strains of different serotypes (FIG. 6). The heterologous stains used to demonstrate the improved breadth of immunity induced by the HEP vaccines isolated from the cells subjected to the double stress, covered both serotypes present in the current commercial 13-valent but not the 7-valent vaccines (serotype 19A) as well serotypes of escape variants not covered by these vaccines and of emerging clinical importance (serotypes 8 and 22F) in pneumococcal disease. The breadth of protective immunity induced by the double stress HEP vaccines was also significantly better than that observed with the use of a whole cell killed vaccine.

Example 4—Improved Induction and Immunogenicity of Stress Proteins in Obligate Anaerobes by Multiple Stress Stimuli Laboratory strains of double toxin mutants of *Clostridium difficile* were grown in TY Medium, pH6.8 at 3rC in a shaking incubator in an atmosphere of H2:C02:N2 (ratio 10:10:80) at 50 rpm to achieve an OD of 0.5-0.7 and the cultures were then subjected to a combination of heat and respiratory stress by incubation at 44° C. for 2 hours in an ambient atmosphere. Samples of the cultures were analysed for the induction of heat shock proteins by SDS-PAGE analysis and Western blotting using standard equipment and protocols (Invitrogen). Heat-shock protein enriched vaccine compositions were prepared using ion exchange chromatography as described in WO 2010/026432 and to immunise groups of mice. The antibody responses again showed improved immune responses mediated by vaccine compositions wherein the immunogenic determinant comprises heat shock protein complexes derived from cultures that had been subjected to both heat and respiratory stress, as assayed by western blotting and titration of the blocking of bacterial adhesion to epithelial cell cultures.

Example 5—Improved Induction of Stress Proteins by Multiple Stress in Fungal Microorganisms

*S. cerevisiae* strain ATCC 20602 was grown in Difco YM growth medium, pH5 at 30° C. in a 5l benchtop BioFlo 310 fermenter (New Brunswick Scientific) at a dissolved oxygen concentration of 30% achieved by an agitation speed of 2-800 rpm. After 24 hours the culture was subjected to a combination of heat and respiratory stress by stopping the oxygen feed and raising the temperature to 40° C. for 1 hour. Samples of the cultures were analysed for the induction of heat shock proteins by SDS-PAGE analysis and Western blotting using standard equipment and protocols (Invitrogen).

The invention claimed is:

1. A method for production of a composition comprising stress protein complexes formed between a stress protein and a peptide, the method comprising:
   (a) culturing cells;
   (b) exposing said cells to at least two stress inducing stimuli of different types wherein a first stress inducing stimulus is heat and a second stress inducing stimulus is respiratory stress or acid based stress,
   wherein the respiratory stress comprises decreasing or increasing the amount of oxygen to which the cells are exposed, and
   wherein the acid based stress comprises reducing the pH of the cells below the pH that causes normal physiological growth or homeostasis of the cells;
   (c) producing stress protein complexes having increased yield and immunogenicity when compared to stress protein complexes produced with exposure to only the first or second stress inducing stimulus;
   (d) lysing the cells to produce a cell lysate;
   (e) clarifying the cell lysate to produce a clarified cell lysate;
   (f) purifying the stress protein complexes from the clarified cell lysate;
   (g) subjecting the clarified cell lysate to purification using ion exchange, wherein the clarified cell lysate is buffered to a pH within 2 units of the pI of the stress protein complexes;
   (h) eluting the stress protein complexes with a salt gradient; and
   (i) obtaining an enriched preparation comprising the stress protein complexes.

2. The method as claimed in claim 1 wherein the heat stress comprises increasing a heat to which the cultured cells are exposed to a temperature of around 5-10° C. greater than a normal growth temperature of the cells.

3. The method as claimed in claim 1 wherein the second stress inducing stimulus is a respiratory stress.

4. The method as claimed in claim 3 wherein the respiratory stress comprises decreasing the amount of oxygen.

5. The method as claimed in claim 3 wherein the cells are exposed to the heat stress prior to being exposed to the respiratory stress, the cells are exposed to the heat stress and to the respiratory stress concurrently or the cells are exposed to the respiratory stress prior to being exposed to the heat stress.

6. The method as claimed in claim 1 wherein the second stress inducing stimulus is an acid based stress.

7. The method as claimed in claim 6 wherein the acid based stress comprises decreasing the pH to 5.5 or lower.

8. The method as claimed in claim 6 wherein the cells are exposed to the heat stress prior to being exposed to the acid based stress, the cells are exposed to the heat stress and to the acid based stress concurrently or the cells are exposed to the acid based stress prior to being exposed to the heat stress.

9. The method as claimed in claim 1 wherein the cells are subjected to the heat stress for a time period ranging from 1 to 2 hours.

10. The method as claimed in claim 1 wherein the cells are selected from the group consisting of pathogenic cells, cancerous cells, cells infected by a pathogenic organism, cells which have been genetically modified to constitutively express heat shock proteins, cells which have been genetically modified to express a heterologous protein which is derived from a cancerous cell and cells which have been genetically modified to express a heterologous protein derived from a pathogen which causes an infectious disease in a host.

11. The method as claimed in claim 10 wherein the cells are pathogenic cells.

12. The method as claimed in claim 11 wherein the pathogenic cells are selected from the group consisting of gram positive prokaryotic cells, gram negative prokaryotic cells, microbial cells, protozoan cells, fungi and parasitic cells.

13. The method as claimed in claim 12 wherein at least one of the gram positive prokaryotic cells and the gram negative prokaryotic cells are selected from the group consisting of *Escherichia, Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasteurella, Moraxella, Acinetobacter, Erysipelothrix, Branhamella, Actinobacillus, Streptobacillus, Listeria, Calymmatobacterium, Brucella, Bacillus, Clostridium, Treponema, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma.*

14. The method as claimed in claim 1 wherein the cells are selected from the group consisting of *Neisseria, Mycobacteria, Saccharomyces* and *Clostridium*.

15. The method as claimed in claim 1 wherein the cells are *Streptococcus*.

16. The method as claimed in claim 1 wherein the peptide is a tumor specific antigen.

17. The method as claimed in claim 1 wherein:
the cells are anaerobic pathogenic cells; and
the respiratory stress comprises increasing an amount of oxygen to which the cultured cells are exposed.

18. The method as claimed in claim 1 wherein the stress protein complexes comprise one or more heat shock proteins selected from the group consisting of hsp20-30 kD, hsp40, hsp60, hsp70, hsp90, hsp100, calrecticulin, hsp72, grp94, grp75 BiP/grp78, grp75/mt and gp96.

19. The method as claimed in claim 1 wherein the stress protein complexes comprise GroEl and DnaK.

20. The method as claimed in claim 1 wherein the stress protein complexes have a molecular weight in a range of 50 KDa to 900 KDa.

21. The method as claimed in claim 11 wherein the pathogenic cells are gram positive prokaryotic cells.

22. The method as claimed in claim 11 wherein the pathogenic cells are gram negative prokaryotic cells.

23. The method as claimed in claim 1 further comprising mixing the stress protein complexes with at least one pharmaceutically acceptable excipient to produce a vaccine composition.

* * * * *